(12) United States Patent
Berg et al.

(10) Patent No.: US 7,056,939 B2
(45) Date of Patent: Jun. 6, 2006

(54) 4-(4METHOXYBENZYL)-N'-(5-NITRO 1,3-THIAZOL-2-YL)UREA AND ITS USE IN THE TREATMENT OF CONDITIONS ASSOCIATED WITH GLYCOGEN-SYNTHASE KINASE-3 (GSK3)

(75) Inventors: Stefan Berg, Södertälje (SE); Sven Hellberg, Södertälje (SE)

(73) Assignee: Astrazeneca AB, Sodertalje (SE)

( * ) Notice: Subject to any disclaimer, the term of this patent is extended or adjusted under 35 U.S.C. 154(b) by 154 days.

(21) Appl. No.: 10/481,711

(22) PCT Filed: Jul. 3, 2002

(86) PCT No.: PCT/SE02/01338

§ 371 (c)(1),
(2), (4) Date: Dec. 22, 2003

(87) PCT Pub. No.: WO03/004478

PCT Pub. Date: Jan. 16, 2003

(65) Prior Publication Data

US 2005/0054698 A1    Mar. 10, 2005

(30) Foreign Application Priority Data

Jul. 5, 2001   (SE) .................... 0102440

(51) Int. Cl.
*A61K 31/427*   (2006.01)
*A61K 31/426*   (2006.01)
*C07D 277/56*   (2006.01)
*C07D 277/58*   (2006.01)

(52) U.S. Cl. ............. 514/371; 548/192; 548/190; 514/370

(58) Field of Classification Search ........... 548/192, 548/190; 514/371, 370
See application file for complete search history.

(56) References Cited

FOREIGN PATENT DOCUMENTS

WO   WO-00/26203       5/2000
WO   WO 200026203 A1 *  5/2000

* cited by examiner

*Primary Examiner*—Kamal A. Saeed
*Assistant Examiner*—Michael P. Barker
(74) *Attorney, Agent, or Firm*—White & Case LLP

(57) ABSTRACT

The present invention relates to a new compound of formula I as a free base or a pharmaceutically acceptable salt thereof, a process for the preparation, pharmaceutical formulations containing said therapeutically active compound and to the use of said compound in therapy.

(I)

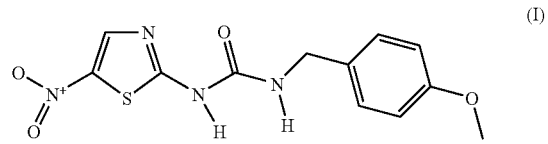

10 Claims, No Drawings

SEQUENCE LISTING

```
<160> NUMBER OF SEQ ID NOS: 1

<210> SEQ ID NO 1
<211> LENGTH: 14
<212> TYPE: PRT
<213> ORGANISM: Unknown
<220> FEATURE:
<223> OTHER INFORMATION: a biotinylated peptide substrate
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (11)..(11)
<223> OTHER INFORMATION: PHOSPHORYLATION
```

-continued

```
<400> SEQUENCE: 1

Ala Ala Glu Glu Leu Asp Ser Arg Ala Gly Ser Pro Gln Leu
1               5                   10
```

4-(4METHOXYBENZYL)-N'-(5-NITRO 1,3-THIAZOL-2-YL)UREA AND ITS USE IN THE TREATMENT OF CONDITIONS ASSOCIATED WITH GLYCOGEN-SYNTHASE KINASE-3 (GSK3)

FIELD OF THE INVENTION

The present invention relates to a new compound of formula I, as a free base or a pharmaceutically acceptable salt thereof, to pharmaceutical formulations containing said compound and to the use of said active compound in therapy. The present invention further relates to a process for the preparation of the compound of formula I.

An object of the invention is to provide a compound of formula I for therapeutic use, especially a compound that is useful for the prevention and/or treatment of conditions associated with glycogen synthase kinase-3 (GSK3) in mammals, including man. Particularly, a compound of formula I exhibiting a selective inhibition of GSK-3.

BACKGROUND OF THE INVENTION

Glycogen synthase kinase 3 (GSK3) is a serine/threonine protein kinase composed of two isoforms ($\alpha$ and $\beta$), which are encoded by distinct genes but are highly homologous within the catalytic domain. GSK3 is highly expressed in the central and peripheral nervous system. GSK3 phosphorylates several substrates including tau, $\beta$-catenin, glycogen synthase, pyruvate dehydrogenase and elongation initiation factor 2b (eIF2b). Insulin and growth factors activate protein kinase B, which phosphorylates GSK3 on serine 9 residue and inactivates it.

Alzheimer's Disease (AD) Dementias, and Taupathies.

AD is characterized by cognitive decline, cholinergic dysfunction and neuronal death, neurofibrillary tangles and senile plaques consisting of amyloid-$\beta$ deposits. The sequence of these events in AD is unclear, but believed to be related. Glycogen synthase kinase 3$\beta$ (GSK3$\beta$) or Tau ($\tau$) phosphorylating kinase selectively phosphorylates the microtubule associated protein $\tau$ in neurons at sites that are hyperphosphorylated in AD brains. Hyperphosphorylated protein $\tau$ has lower affinity for microtubules and accumulates as paired helical filaments, which are the main components that constitute neurofibrillary tangles and neuropil threads in AD brains. This results in depolymerization of microtubules, which leads to dying back of axons and neuritic dystrophy. Neurofibrillary tangles are consistently found in diseases such as AD, amyotrophic lateral sclerosis, parkinsonism-dementia of Gaum, corticobasal degeneration, dementia pugilistica and head trauma, Down's syndrome, postencephalatic parkinsonism, progressive supranuclear palsy, Niemann-Pick's Disease and Pick's Disease. Addition of amyloid-$\beta$ to primary hippocampal cultures results in hyperphosphorylation of $\tau$ and a paired helical filaments-like state via induction of GSK3$\beta$ activity, followed by disruption of axonal transport and neuronal death (Imahori and Uchida., J. Biochem 121:179–188, 1997). GSK3$\beta$ preferentially labels neurofibrillary tangles and has been shown to be active in pre-tangle neurons in AD brains. GSK3 protein levels are also increased by 50% in brain tissue from AD patients. Furthermore, GSK3$\beta$ phosphorylates pyruvate dehydrogenase, a key enzyme in the glycolytic pathway and prevents the conversion of pyruvate to acetyl-Co-A (Hoshi et al., PNAS 93:2719–2723, 1996). Acetyl-Co-A is critical for the synthesis of acetylcholine, a neurotransmitter with cognitive functions. Thus, GSK3$\beta$ inhibition may have beneficial effects in progression as well as the cognitive deficits associated with Alzheimer's disease and other above-referred to diseases.

Chronic and Acute Neurodegenerative Diseases

Growth factor mediated activation of the PI3K/Akt pathway has been shown to play a key role in neuronal survival. The activation of this pathway results in GSK3$\beta$ inhibition. Recent studies (Bhat et. al., PNAS 97:11074–11079 (2000)) indicate that GSK3$\beta$ activity is increased in cellular and animal models of neurodegeneration such as cerebral ischemia or after growth factor deprivation. For example, the active site phosphorylation was increased in neurons vulnerable to apoptosis, a type of cell death commonly thought to occur in chronic and acute degenerative diseases such as Alzheimer's Disease, Parkinson's Disease, amyotrophic lateral sclerosis, Huntington's Disease and HIV dementia, ischemic stroke and head trauma. Lithium was neuroprotective in inhibiting apoptosis in cells and in the brain at doses that resulted in the inhibition of GSK3$\beta$. Thus GSK3$\beta$ inhibitors could be useful in attenuating the course of neurodegenerative diseases.

Bipolar Disorders (BD)

Bipolar Disorders are characterised by manic episodes and depressive episodes. Lithium has been used to treat BD based on its mood stabilising effects. The disadvantage of lithium is the narrow therapeutic window and the danger of overdosing that can lead to lithium intoxication. The recent discovery that lithium inhibits GSK3 at therapeutic concentrations has raised the possibility that this enzyme represents a key target of lithium's action in the brain (Stambolic et al., Curr. Biol. 6:1664–1668, 1996; Klein and Melton; PNAS 93:8455–8459, 1996). Inhibition of GSK3$\beta$ may therefore be of therapeutic relevance in the treatment of BD as well as in AD patients that have affective disorders.

Schizophrenia

GSK3 is involved in signal transduction cascades of multiple cellular processes, particularly during neural development. Kozlovsky et al (Am J Psychiatry 2000 May; 157(5):831–3) found that GSK3$\beta$ levels were 41% lower in the schizophrenic patients than in comparison subjects. This study indicates that schizophrenia involves neurodevelopmental pathology and that abnormal GSK3 regulation could play a role in schizophrenia. Furthermore, reduced $\beta$-catenin levels have been reported in patients exhibiting schizophrenia (Cotter et al., Neuroreport 9:1379–1383 (1998)).

Diabetes

Insulin stimulates glycogen synthesis in skeletal muscles via the dephosphorylation and thus activation of glycogen synthase. Under resting conditions, GSK3 phosphorylates and inactivates glycogen synthase via dephosphorylation. GSK3 is also over-expressed in muscles from Type II diabetic patients (Nikoulina et al., Diabetes 2000 February; 49(2):263–71). Inhibition of GSK3 increases the activity of glycogen synthase thereby decreasing glucose levels by its conversion to glycogen. GSK3 inhibition may therefore be of therapeutic relevance in the treatment of Type I and Type II diabetes and diabetic neuropathy.

Hair Loss

GSK3 phosphorylates and degrades $\beta$-catenin. $\beta$-catenin is an effector of the pathway for keratonin synthesis. $\beta$-catenin stabilisation may be lead to increase hair development. Mice expressing a stabilised $\beta$-catenin by mutation of sites phosphorylated by GSK3 undergo a process resembling de novo hair morphogenesis (Gat et al., Cell Nov. 25, 1998; 95 (5):605–14)). The new follicles formed sebaceous glands and dermal papilla, normally established only in embryogenesis. Thus GSK3 inhibition may offer treatment for baldness.

Oral Contraceptives

Vijajaraghavan et al. (Biol Reprod 2000 June; 62 (6): 1647–54) reported that GSK3 is high in motile versus immotile sperm. Immunocytochemistry revealed that GSK3 is present in the flagellum and the anterior portion of the sperm head. These data suggest that GSK3 could be a key element underlying motility initiation in the epididymis and regulation of mature sperm function. Inhibitors of GSK3 could be useful as contraceptives for males.

DISCLOSURE OF THE INVENTION

The object of the present invention is to, provide a compound having a selective inhibiting effect at GSK3 as well as having a good bioavailability.

Accordingly, the present invention provides a compound of formula I:

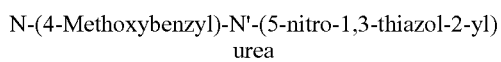

as a free base or a pharmaceutically acceptable salt thereof.

A suitable pharmaceutically acceptable salt of the compound of the invention is, for example, an acid-addition salt, which is sufficiently basic, such as an inorganic or organic acid or an alkali metal salt, an alkaline earth metal salt.

The compound of formula I may be administered in the form of a pro-drug, which is broken down in the human or animal body to give the compound of formula I.

It is also to be understood that the compound of formula I can exist in the solvated form such as the hydrated form, as well as in the unsolvated form. It is to be understood that the invention encompasses all such forms.

Methods of Preparation

Another aspect of the present invention provides a process for preparing the compound of formula I as a free base or a pharmaceutically acceptable salt thereof.

The process for the preparation of the compound of formula I comprises of:

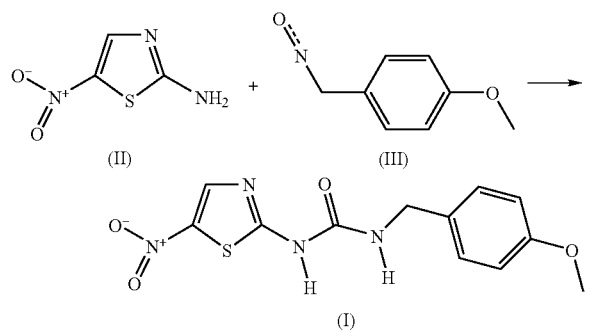

reacting a compound of formula II with a compound of formula III in a suitable solvent such as N,N-dimethylformamide, dimethyl sulfoxide, dioxane or tetrahydrofuran at a temperature within the range of +70 to +150° C.

EXAMPLE 1

N-(4-Methoxybenzyl)-N'-(5-nitro-1,3-thiazol-2-yl) urea

A mixture of 2-amino-5-nitrothiazole (0.89 g, 6.13 mmol) and 4-methoxybenzylisocyanate (1 g, 6.13 mmol) in N,N-dimethylformamide (6 mL) was heated at 100° C. under nitrogen atmosphere for 15 h. The mixture was allowed to cool and was partitioned between water and ethyl acetate. The aqueous layer was extracted with another portion of ethyl acetate. The combined organic layers were washed with brine, dried ($MgSO_4$) and evaporated to give 2.5 g of a semi-solid crude product. Most of the material was dissolved in chloroform/ethanol (98:2, approx. 15 mL) and triethylamine (3 mL) followed by filtration. The dissolved crude product was purified on a silica gel column using $CHCl_3$/Etanol, 95:5 as the eluent to give 408 mg (22% yield) of the title compound as a yellowish solid: mp > 190° C. (decomp.); $^1H$ NMR (DMSO-$d_6$, 400 MHz) δ 11.64 (br s, 1 H), 8.50 (s, 1 H), 7.25–7.23 (m, 3 H), 6.92–6.89 (m, 2 H), 4.30 (d, J=5.9 Hz, 2 H), 3.73 (s, 3 H); $^{13}C$NMR (DMSO-$d_6$, 100 MHz) δ 164.42, 158.43, 153.48, 143.47, 140.80, 130.82, 128.72, 113.82, 55.08, 42.60; ESMS m/z 309 ($M^+$+1).

Pharmaceutical Formulations

According to one aspect of the present invention there is provided a pharmaceutical formulation comprising the compound of formula I, as a free base or a pharmaceutically acceptable salt thereof, for use in the prevention and/or treatment of conditions associated with glycogen synthase kinase-3.

The formulation may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration as an ointment, patch or cream or for rectal administration as a suppository.

In general the above formulations may be prepared in a conventional manner using pharmaceutically acceptable carriers and diluents.

Suitable daily doses of the compound of formula I in the treatment of a mammal, including man are approximately 0.01 to 250 mg/kg bodyweight at peroral administration and about 0.001 to 250 mg/kg bodyweight at parenteral administration. The typical daily dose of the active ingredient varies within a wide range and will depend on various factors such as the relevant indication, the route of administration, the age, weight and sex of the patient and may be determined by a physician.

Medical Use

Surprisingly, it has been found that the compound of the present invention, as a free base or a pharmaceutically acceptable salt thereof, is well suited for inhibiting glycogen synthase kinase-3 (GSK3). Accordingly, the compound of the present invention is expected to be useful in the prevention and/or treatment of conditions associated with glycogen synthase kinase-3 activity, i.e. the compound may be used to produce an inhibitory effect of GSK3 in mammals, including man, in need of such prevention and/or treatment.

GSK3 is highly expressed in the central and peripheral nervous system and in other tissues. Thus, it is expected that the compound of the invention is well suited for the prevention and/or treatment of conditions associated with glycogen synthase kinase-3 in the central and peripheral nervous system. In particular, the compound of the invention is expected to be suitable for prevention and/or treatment of one or more conditions such as dementia, Alzheimer's Disease, Parkinson's Disease, Frontotemporal dementia Parkinson's Type, Parkinson dementia complex of Gaum, HIV dementia, diseases with associated neurofibrillar tangle pathologies, amyotrophic lateral sclerosis, corticobasal degeneration, dementia pugilistica, Down's syndrome, Huntington's Disease, postencephelatic parkinsonism, progressive supranuclear palsy, Pick's Disease; Niemann-Pick's Disease, stroke, head trauma and other chronic neurodegenerative diseases, Bipolar Disease, affective disorders, depression, schizophrenia, cognitive disorders, Type I and Type II diabetes and diabetic neuropathy, hair loss and contraceptive medication.

The dose required for the therapeutic or preventive treatment of a particular disease will necessarily be varied depending on the host treated, the route of administration and the severity of the illness being treated.

The present invention relates also to the use of the compound of formula I, in the manufacture of a medicament for the prevention and/or treatment of conditions associated with GSK3.

In the context of the present specification, the term "therapy" includes treatment as well as prevention, unless there are specific indications to the contrary. The terms "therapeutic" and "therapeutically" should be construed accordingly.

The invention also provides a method of treatment and/or prevention of conditions associated with GSK3, in a patient suffering from, or at risk of said condition, which comprises administering to the patient an effective amount of the compound of formula I.

Non-Medical Use

In addition to their use in therapy, the compound of formula I, as a free base or a pharmaceutically acceptable salt thereof, is also useful as a pharmacological tool in the development and standardisation of in vitro and in vivo test systems for the evaluation of the effects of inhibitors of GSK3 in laboratory animals such as cats, dogs, rabbits, monkeys, rats and mice, as part of the search for new therapeutical agents.

Pharmacology

Determination of ATP Competition in Scintillation Proximity GSK3β Assay.

GSK3β Scintillation Proximity Assay.

The competition experiments were carried out in duplicate with 10 different concentrations of the inhibitors in clear-bottom microtiter plates (Wallac, Finland). A biotinylated peptide substrate, Biotin-Ala-Ala-Glu-Glu-Leu-Asp-Ser-Arg-Ala-Gly-Ser($PO_3H_2$)-Pro-Gln-Leu (SEQ ID NO: 1) (AstraZeneca, Lund), was added at a final concentration of 1 μM in an assay buffer containing 1 mU recombinant human GSK3β (Dundee University, UK), 12 mM morpholinepropanesulfonic acid (MOPS), pH 7.0, 0.3 mM EDTA, 0.01% β-mercaptoethanol, 0.004 % Brij 35 (a phosphatase inhibitor), 0.5% glycerol and 0.5 μg BSA/25 μl. The reaction was initiated by the addition of 0.04 μCi [γ-$^{33}$P]ATP (Amersham, UK) and unlabelled ATP at a final concentration of 1 μM and assay volume of 25 μl. After incubation for 20 minutes at room temperature, each reaction was terminated by the addition of 25 μl stop solution containing 5 mM EDTA, 50 μM ATP, 0.1 % Triton X-100 and 0.25 mg streptavidin coated Scintillation Proximity Assay (SPA) beads (Amersham, UK). After 6 hours the radioactivity was determined in a liquid scintillation counter (1450 MicroBeta Trilux, Wallac). The inhibition curves were analysed by non-linear regression using GraphPad Prism, USA. The $K_m$ value of ATP for GSK3β, used to calculate the inhibition constants ($K_i$) of the various compounds, was 20 μM.

The following abbreviations have been used:

| | |
|---|---|
| MOPS | Morpholinepropanesulfonic acid |
| EDTA | Ethylenediaminetetraacetic acid |
| BSA | Bovin Serum Albumin |
| ATP | Adenosine Triphophatase |
| SPA | Scintillation Proximity Assay |
| GSK3 | Glycogen synthase kinase 3 |

Results

The $K_i$ value for the compound of the present invention is 96 nM.

The invention claimed is:

1. A compound of formula I

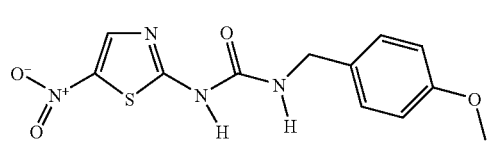

(I)

in the form of a free base or a pharmaceutically acceptable salt thereof.

2. A pharmaceutical formulation comprising as active ingredient a therapeutically effective amount of the compound of claim 1 in association with pharmaceutically acceptable carriers or diluents.

3. A method for the inhibition or treatment of a medical condition associated with glycogen synthase kinase-3, the method comprising administering to a patient in need of such inhibition or treatment a therapeutically effective amount of the compound or salt thereof as defined in claim 1, wherein the condition is dementia or Alzheimer's Disease.

4. A process for the preparation of the compound of formula I, the process comprising reacting the compound of formula II with the compound of formula III.

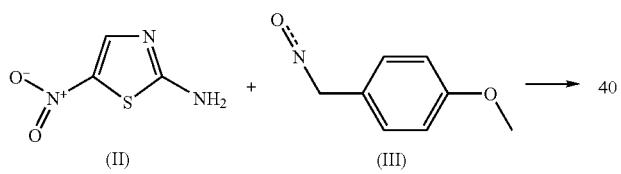

(II)       (III)

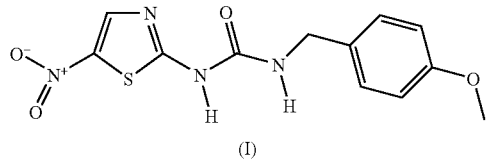

(I)

5. The method according to claim 3, wherein the compound is administered perorally.

6. The method according to claim 5, wherein the therapeutically effective daily dosage is about 0.01 to about 250 mg/kg.

7. The method according to claim 3, wherein the compound is administered parenterally.

8. The method according to claim 7, wherein the therapeutically effective daily dosage is about 0.001 to about 250 mg/kg.

9. The process according to claim 4, wherein a compound of formula II is reacted with a compound of formula III in a solvent at a temperature from about +70° C. to about +150° C.

10. The process according to claim 4 or 9, wherein the solvent is N,N-dimethylformamide, dimethyl sulfoxide, dioxane or tetrahydrofuran.

* * * * *